United States Patent [19]

Bortolaso et al.

[11] Patent Number: 5,710,321

[45] Date of Patent: Jan. 20, 1998

[54] PROCESS FOR PREPARING THE CYCLOHEXYLAMINE SALT OF (+)-THREO-2-HYDROXY-3-(2'-AMINOPHENYLTHIO)-3-(4"-METHOXYPHENYL)-PROPIONIC ACID AND OF ITS (-)-ANTIPODE"

[75] Inventors: Roberto Bortolaso; Siro Serafini, both of Vicenza, Italy

[73] Assignee: F.I.S. Fabbrica Italiana Sintetici S.p.A., Italy

[21] Appl. No.: 632,077

[22] Filed: Apr. 15, 1996

[30] Foreign Application Priority Data

May 11, 1995 [IT] Italy .................. MI95A0948

[51] Int. Cl.[6] .................................. C07C 55/00
[52] U.S. Cl. ........................... 562/401; 562/431
[58] Field of Search ......................... 562/401, 431

[56] References Cited

U.S. PATENT DOCUMENTS

| | | | |
|---|---|---|---|
| 4,931,587 | 6/1990 | Piselli | 562/401 |
| 4,939,295 | 7/1990 | Merli et al. | 562/401 |
| 5,183,922 | 2/1993 | Rizzi et al. | 560/7 |

*Primary Examiner*—Samuel Barts
*Attorney, Agent, or Firm*—Diller, Ramik & Wight, PC

[57] ABSTRACT

The present invention relates to a process for preparing the cyclohexylamine salt of (+)-threo-2-hydroxy-3-(2'-aminophenylthio)-3-(4"-methoxyphenyl)-propionic acid and of its optical (–)-antipode, by starting from the racemate acid by means of a first crystallization from a suitable chiral base and a second crystallization from a cyclohexylamine-containing solvent. Said salt is an intermediate in the synthesis of diltiazem, a well-known calcium-antagonist drug.

5 Claims, No Drawings

PROCESS FOR PREPARING THE CYCLOHEXYLAMINE SALT OF (+)-THREO-2-HYDROXY-3-(2'-AMINOPHENYLTHIO)-3-(4"-METHOXYPHENYL)-PROPIONIC ACID AND OF ITS (-)-ANTIPODE"

The present invention relates to a novel process for preparing the cyclohexylamine salt of (+)-threo-2-hydroxy-3-(2'-aminophenylthio)-3-(4"-methoxyphenyl)-propionic acid of Formula (I) and of its (−) optical antipode of Formula (II):

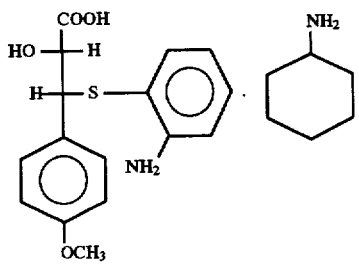

[2S, 3S]

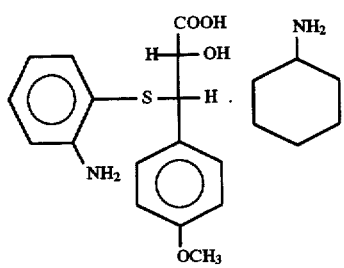

[2R, 3R]

Both these salts are used according to Italian Patent No. 1,237,785 as initiators in a process for enantiomeric separation based on direct crystallization of cyclohexylamine salt of (+)- and (−)-forms of racemate threo-2-hydroxy-3-(2'-amino-phenylthio)-3-(4"-methoxyphenyl)-propionic acid, in the following referred to as "threo acid" for the sake of brevity.

The salt of (+)-threo acid can be used, according to known techniques (see, e.g., same Italian Patent No. 1,237,785 and also Italian Patent No. 1,237,204) for the synthesis of a calcium-antagonist drug used in various forms of cardiac decompensation and failure, having the generic name "diltiazem", i.e., (+)-2-(4'-methoxyphenyl)-3-acetoxy-5-[2-(dimethyl-amino)-ethyl]-cis-2,3-dihydro-1,5-benzothiazepin-4-(5H)-one hydrochloride of Formula (III)

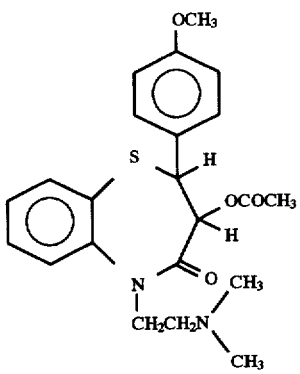

According to the prior art, preparing this salt would be a relatively time-consuming and laborious task, because it implies a four-step synthesis, i.e.:

1) enantiomeric separation of racemic threo acid by salification with a selective chiral base (e.g., with alpha-phenyl-ethyl-amine) and fractional crystallization. Molar yield is of approximately 40–45%.
2) Isolating the free threo acid by acidification, removal of chiral base and crystallization of (+)-threo or (−)-threo acid. The overall yield decreases down to 35–40%. Unfortunately, threo acid contains an amino group which easily yields salts which are poorly soluble in an acidic environment, and precipitate as impurities, polluting the desired product. Therefore, a further re-crystallization is necessary.
3) Said re-crystallization reduces the overall yield down to 30-35%. Now, a pure acid free from its salts is obtained which however shows a lower enantiomeric purity because the solubility of enantiomeric acid is by far higher than of racemic acid.
4) Finally, (+)-threo or (−)-threo acid is salified with cyclohexylamine and the resulting product is isolated from a suitable solvent. The overall yield is of 25–30% relatively to the racemic threo acid.

The product normally shows a high enantiomeric ratio, higher than 90:10.

Now, the purpose of the present invention is of obtaining, according to a simple, fast process, and with high yield, a suitable product for use disclosed in Italian Patent No. 1,237,785. In this patent, cyclohexylamine salt is used as the initiator in the process of separation of racemic threo acid; an enantiomerically enriched salt is required; however, an enantiomeric ratio of 60:40 is enough. Therefore, using a very selective chiral base, as, e.g., alpha-phenyl-ethyl-amine, is not advantageous in the present case, because it supplies a yield which is of 40–45% at maximum during the first enantiomeric separation step.

According to the present invention, the present Applicant has found now that 1-cyclohexylethylamine, available from the market as either the (+)- or the (−)-enantiomer, supplies an enantiomerically enriched product (with an enantiomeric ratio of 70:30) with a much higher yield, i.e., of approximately 70%.

According to the present invention, the present Applicant surprisingly found also that after the fractional crystallization of racemic threo acid with the chiral base, the resulting salt can be directly treated, without even drying it, with an excess of cyclohexylamine in a suitable solvent, with the crystallization of the desired product, i.e., of cyclohexylamine salt of (+)-threo or (−)-threo acid being obtained in a yield of approximately 80%.

Therefore, the overall yield is of 50–60% relatively to the racemic threo acid and the product displays an enantiomeric ratio of round 70:30, which is perfectly suitable for the purpose of the present invention as summarized hereinabove.

The advantage offered by the present invention will be clear from the matter of fact that, as compared to the prior art, the yield of the process according to the present invention is nearly twice as high, and in lieu of four synthesis steps, only two steps are necessary.

According to a typical embodiment of the invention, supplied for exemplifying, non-limitative purposes, 1 mol of racemic threo acid is reacted in 3–12 parts by volume (preferably 10 parts by volume) of alcohol or alcohol/water mixture (preferably denatured ethyl alcohol) with 0.5–1.5 mol (preferably approximately 1.1. mol) of chiral base, i.e., (+)- or (−)-1-cyclohexylethylamine, possibly completing the neutralization with an achiral base (e.g., sodium hydroxide or tri-ethylamine). The reaction mixture is heated until all

3 solids are dissolved and then is cooled until a suitable crystallization is obtained (e.g., 4–5 hours at 0° C.).

The so obtained product is filtered and recrystallized (preferably without being dried) from 3–12 parts by volume (preferably 10 volumes) of an alcohol:cyclohexylamine mixture (preferably consisting of 50% methyl alcohol and 50% cyclohexylamine).

The reaction is cooled (for example, 2–3 hours at 0° C.), the precipitate product is filtered off and is dried, with 0.5–0.6 mol of cyclohexylamine salt of (+)-threo or (−)-threo acid being obtained, according to whether (+)-cyclohexylethylamine or (−)-cyclohexylethylamine was used. The enantiomeric ratio is normally comprised within the range of from 70:30 to 75:25.

The following examples illustrate the invention without limiting its purview.

EXAMPLE 1

Salt of (+)-cyclohexylethylamine of (+)-threo acid

Three hundred and twenty ml of denatured ethanol, 32 c of racemic threo acid (purity 98%) and 15 ml of (+)-1-cyclohexylethylamine are charged to a 3-necked flask of 1 litre of capacity, equipped with heating bath, stirrer, thermometer and bubble condenser. The solids are dissolved by keeping the mixture refluxing over 30 minutes and the resulting solution is cooled down to 0° C. during 1 hour. After crystallization, the mixture is kept at 0° C. for 5 hours.

The crystallized solid is filtered off and washed with 32 ml of denatured ethanol; 32.6 g of moist product is obtained which is used as such in following Example 2.

The yield is of approximately 70% and the enantiomeric ratio (HPLC) is of 75.3:24.7.

EXAMPLE 2

Cyclohexylamine salt of (+)-threo acid

An amount of 32.6 g of moist product from Example 1, 150 ml of methanol and 150 ml of cyclohexylamine are charged to a 3-necked flask of 1 litre of capacity, equipped with heating bath, stirrer, thermometer and bubble condenser. The reaction mixture is heated under refluxing conditions until all solids have got dissolved and the resulting solution is cooled down to 0° C. over 2 hours.

The precipitated solids are filtered off. The filter cake is washed with 30 ml of 1:1 methanol:cyclohexylamine blend and is dried; 22 g of product is obtained.

The yield is of about 80% and the overall yield over racemic threo acid is of 53.5%.

The enantiomeric ratio (HPLC) is of 76.7/23.3.

EXAMPLE 3

(−)-Cyclohexylethylamine salt of (−)-threo acid

Three hundred and twenty ml of denatured ethanol, 32 g of racemic threo acid (purity 98%) and 15 ml of (−)-1-cyclohexylethylamine are charged to a 3-necked flask of 1 litre of capacity, equipped with heating bath, stirrer, thermometer and bubble condenser. The solids are dissolved by keeping the mixture refluxing over 30 minutes and the resulting solution is cooled down to 0° C. during 1 hour. After crystallization, the mixture is kept at 0° C. for 5 hours.

The crystallized solid is filtered off and washed with 32 ml of denatured ethanol; 35.9 g of moist product is obtained which is used as such in Example 4.

The yield is of approximately 70% and the enantiomeric ratio (HPLC) is of 37.5:62.5.

4

EXAMPLE 4

Cyclohexylamine salt of (−)-threo acid

An amount of 35.9 g of moist product from Example 3, 150 ml of methanol and 150 ml of cyclohexylamine are charged to a 3-necked flask of 1 litre of capacity, equipped with heating bath, stirrer, thermometer and bubble condenser. The reaction mixture is heated under refluxing conditions until all solids have got dissolved and the resulting solution is cooled down to 0° C. over 2 hours.

The precipitated solids are filtered off. The filter cake is washed with 30 ml of 1:1 methanol:cyclohexylamine blend and is dried; 24 g of product is obtained.

The yield is of about 80% and the overall yield over racemic threo acid is of 58.4%.

The enantiomeric ratio (HPLC) is of 30.3/69.7.

EXAMPLE 5

Cyclohexylamine salt of (+)-threo acid (recrystallization)

Ten g of product from Example 2 and 100 ml of methanol are charged to a 3-necked flask of 250 ml of capacity, equipped with heating bath, stirrer, thermometer and bubble condenser. The solids are dissolved by refluxing the reaction mixture, then the reaction mixture is cooled down to 0° C. and is kept at that temperature over 2 hours, is filtered, the filter cake is washed with 10 ml of methanol and is dried.

The procedure is further repeated twice and at the end 2.6 g of product with an enantiomeric ratio (HPLC) of 99.7/0.3 is obtained.

EXAMPLE 6

Cyclohexylamine salt of (+)-threo acid (direct separation)

An amount of 5.6 g of product from Example 2 and 19.4 g of cyclohexylamine salt of racemic threo acid, equivalent to a mixture of 3 g of (+)-salt and 22 g of racemic salt, are charged to a 3-necked flask of 250 ml of capacity, equipped with heating bath, stirrer, thermometer and bubble condenser. A volume of 200 ml of DMF is added and a clear solution is obtained by heating at 75° C.

The solution is cooled down to 30° C., is seeded with 0.2 g of product from Example 5 and is cooled down to 20° C. After crystallization completion, the resulting mixture is filtered, the filter cake is washed with 10 ml of isopropanol and is dried; 5.9 g of product is obtained with an enantiomeric ratio of 99.6/0.4.

We claim:

1. A process for preparing the cyclohexylamine salt of (+)-threo-2-hydroxy-3-(2'-aminophenylthio)-3-(4"-methoxyphenyl)-propionic acid and of its (−)-antipode, which comprises the steps of:

a) reacting said threo acid in racemic form with the chiral base (+)-1-cyclohexylethylamine or its (−)-1-cyclohexylethylamine enantiomer to form the corresponding (+)- or (−)-1-cyclohexylethylamine salt thereof, and b) reacting said cyclohexylethylamine salt formed in step a) with cyclohexylamine to form the corresponding cyclohexylamine salt of (+)- or, respectively, (−)-threo-2-hydroxy-3-(2'-aminophenylthio)-3-(4"-methoxyphenyl)-propionic acid.

2. The process according to claim 1, characterized in that the (+)-cyclohexylethylamine salt of (+)-threo acid is prepared by reacting said racemic threo acid with (+)-1-cyclohexylethylamine, and in that said (+)-cyclohexylethylamine salt is reacted with cyclohexylamine, thus yielding the cyclohexylamine salt of said (+)-threo acid.

3. The process according to claim 1, characterized in that the (−)-cyclohexylethylamine salt of (−)-threo acid is prepared by reacting said racemic threo acid with (−)-1-cyclohexylethylamine, and in that said (−)-cyclohexylethylamine salt is reacted with cyclohexylamine, thus yielding the cyclohexylamine salt of said (−)-threo acid.

4. The process according to claim 1, wherein said racemic threo acid is reacted in alcohol or in an alcohol/water blend with (+)- or (−)-1-cyclohexylethylamine, with the neutralization reaction optionally being brought to completion with an achiral base, wherein the reaction mixture is heated until all of the solids in the reaction mixture have dissolved, wherein the reaction mixture is then cooled until a crystallization of either said (+)-1-cyclohexylethylamine salt or said (−)-1-cyclohexylethylamine salt of said (+)-threo acid or, respectively, of said (−)-threo acid is obtained, wherein said (+)- or (−)-1-cyclohexylethylamine salt is filtered and recrystallized with an alcohol/cyclohexylamine mixture, wherein the resulting reaction mixture is cooled to form a precipitate of the cyclohexylamine salt of (+)-threo or (−)-threo acid, depending on whether (+)-1-cyclohexylethylamine or (−)-1-cyclohexylethylamine was used to form the cyclohexylethylamine salt of (+)-threo acid or (−)-threo acid, and wherein the precipitated solids are filtered and are dried.

5. Salt of (+)-, or (−)-cyclohexylethylamine of (+)-threo-2-hydroxy-3-(2'-aminophenylthio)-3-(4"-methoxyphenyl)-propionic acid, or of its (−)-antipode, as an intermediate in the synthesis of the cyclohexylamine salt of said (+)- or (−)-threo acid.

* * * * *